(12) United States Patent
Mark et al.

(10) Patent No.: US 9,144,372 B2
(45) Date of Patent: Sep. 29, 2015

(54) SURGICAL ADAPTER ASSEMBLY FOR USE WITH ENDOSCOPE

(75) Inventors: Joseph L. Mark, Indianapolis, IN (US); Brian C. Dougherty, Terre Haute, IN (US); Chad LaMar, Indianapolis, IN (US)

(73) Assignee: Nico Corporation, Indianapolis, IN (US)

( * ) Notice: Subject to any disclaimer, the term of this patent is extended or adjusted under 35 U.S.C. 154(b) by 324 days.

(21) Appl. No.: 12/941,384

(22) Filed: Nov. 8, 2010

(65) Prior Publication Data

US 2011/0112359 A1 May 12, 2011

Related U.S. Application Data

(60) Provisional application No. 61/258,922, filed on Nov. 6, 2009.

(51) Int. Cl.
*A61B 1/00* (2006.01)
*A61B 1/018* (2006.01)
*A61B 17/32* (2006.01)

(52) U.S. Cl.
CPC ............. *A61B 1/018* (2013.01); *A61B 1/00128* (2013.01); *A61B 1/00133* (2013.01); *A61B 17/32002* (2013.01)

(58) Field of Classification Search
USPC .............. 600/102, 104–107, 127, 129–132, 600/153–154; 606/1, 167–183, 205–209
See application file for complete search history.

(56) References Cited

U.S. PATENT DOCUMENTS

| 5,882,294 | A | 3/1999 | Storz et al. | |
|---|---|---|---|---|
| 6,171,234 | B1 | 1/2001 | White et al. | |
| 8,317,689 | B1 | 11/2012 | Remijan et al. | |
| 2002/0022764 | A1* | 2/2002 | Smith et al. | 600/114 |
| 2005/0090835 | A1 | 4/2005 | Deal et al. | |
| 2005/0096504 | A1 | 5/2005 | Akiba | |
| 2005/0182292 | A1 | 8/2005 | Suzuki | |
| 2005/0228346 | A1 | 10/2005 | Goode et al. | |
| 2005/0272976 | A1* | 12/2005 | Tanaka et al. | 600/114 |
| 2006/0241343 | A1 | 10/2006 | Miller et al. | |
| 2007/0270640 | A1 | 11/2007 | Dimitriou et al. | |
| 2008/0064920 | A1 | 3/2008 | Bakos et al. | |
| 2009/0105536 | A1 | 4/2009 | Honda et al. | |
| 2009/0221873 | A1* | 9/2009 | McGrath | 600/153 |
| 2014/0088456 | A1 | 3/2014 | Wang et al. | |

FOREIGN PATENT DOCUMENTS

| DE | 20 2006 012303 U1 | 10/2006 | |
|---|---|---|---|
| JP | 07178098 A | 7/1995 | |
| JP | 09000492 A * | 1/1997 | ............... A61B 1/00 |

(Continued)

OTHER PUBLICATIONS

PCT International Search Report for PCT/US2010/055832 dated Apr. 6, 2011.

(Continued)

*Primary Examiner* — Ryan Henderson
(74) *Attorney, Agent, or Firm* — Kristin L. Murphy; Brooks Kushman P.C.

(57) ABSTRACT

Adapters for properly positioning a portion of a medical instrument that is positioned within an endoscope at site of interest is disclosed.

17 Claims, 16 Drawing Sheets

(56) References Cited

FOREIGN PATENT DOCUMENTS

| | | | |
|---|---|---|---|
| WO | 2009015394 | A1 | 1/2009 |
| WO | 2011057193 | A1 | 5/2011 |
| WO | 2012033760 | A1 | 3/2012 |

OTHER PUBLICATIONS

PCT Partial International Search Report for PCT/US2010/055832 dated Feb. 14, 2011.
PCT International Search Report & Opinion dated Aug. 25, 2014 for PCT/US2014/014816.

* cited by examiner

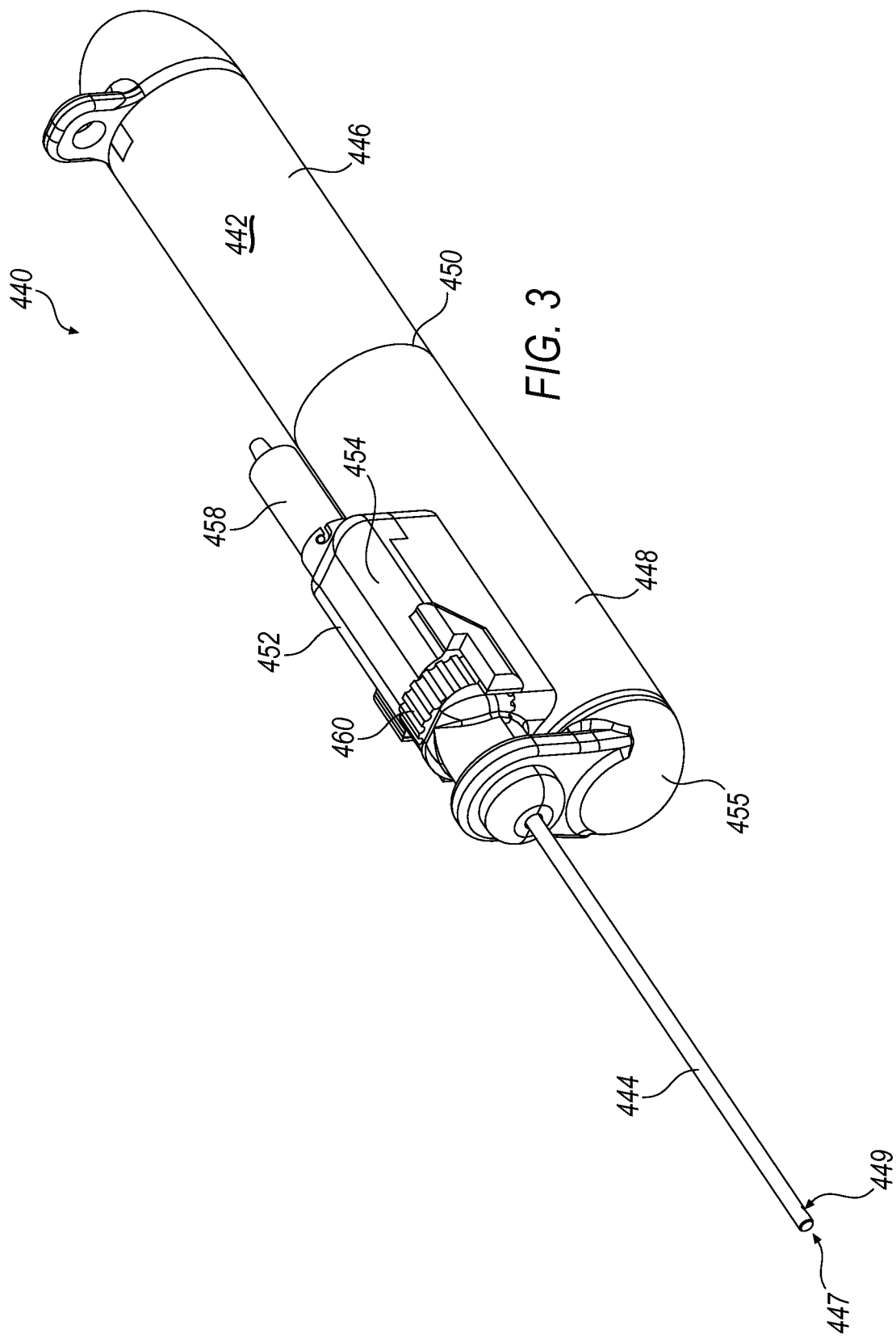

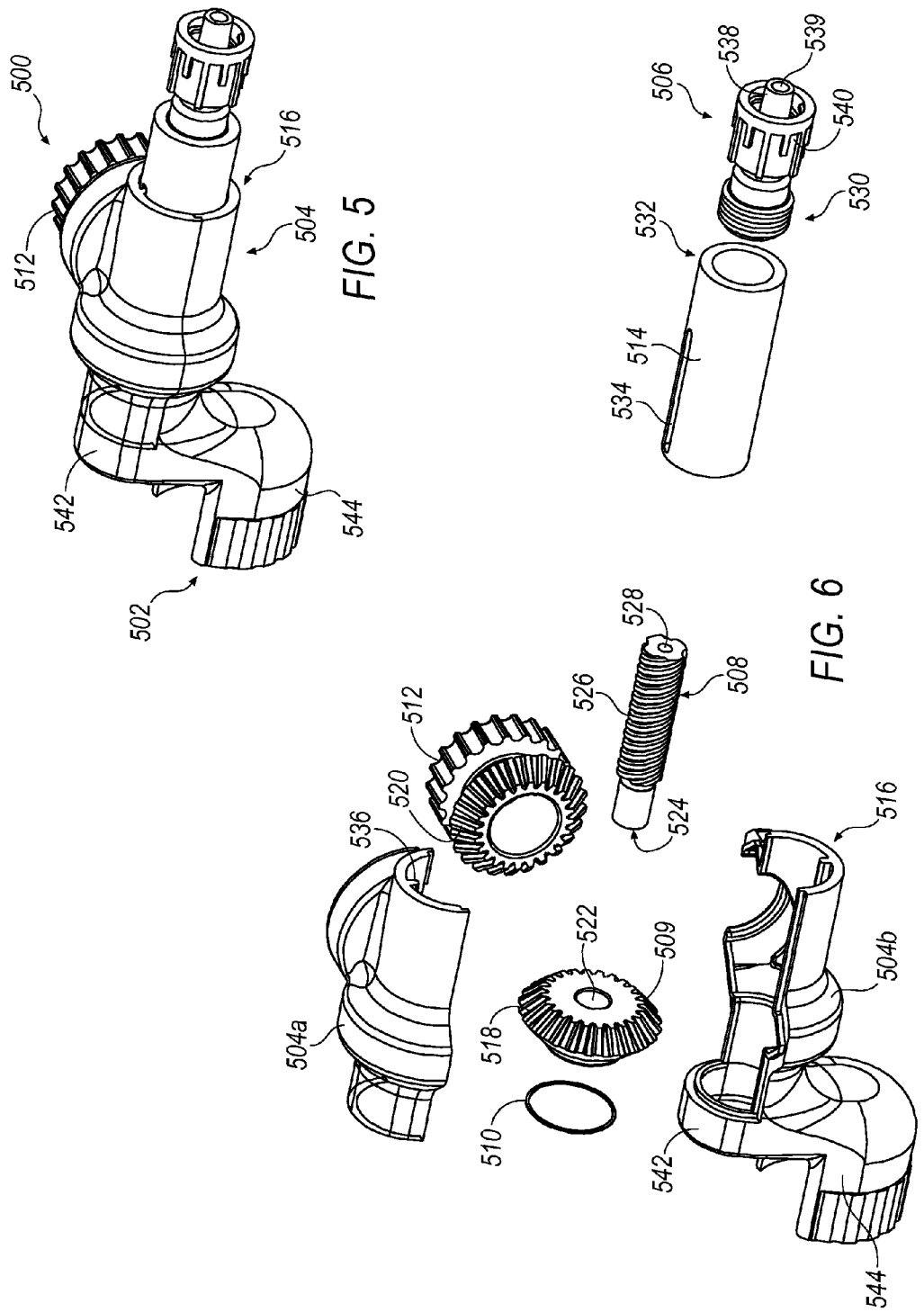

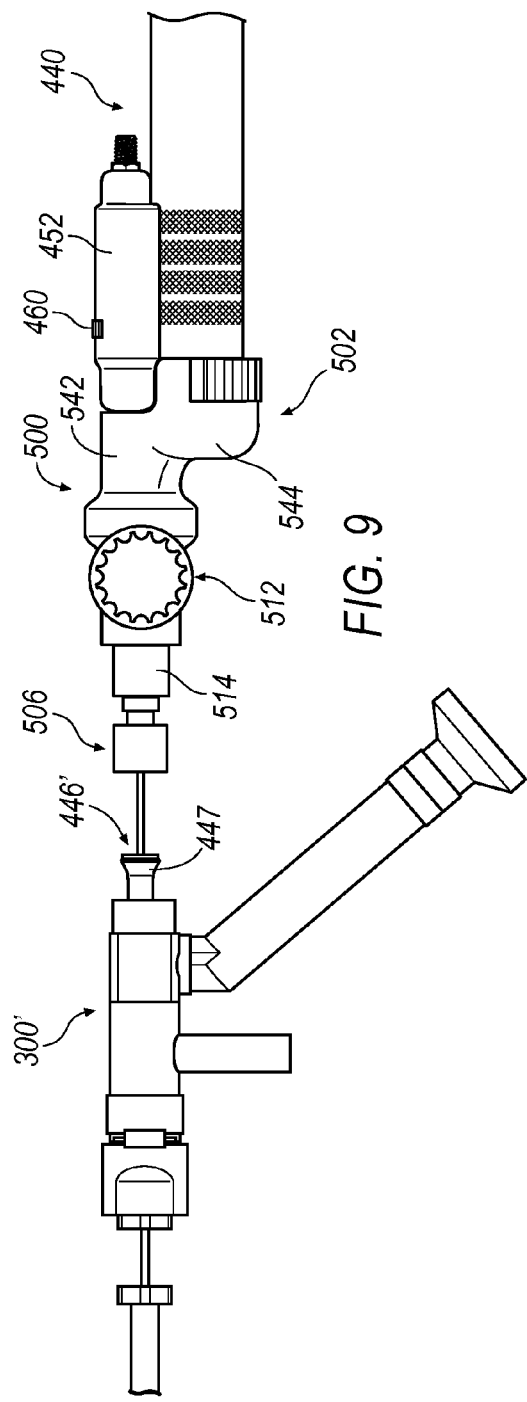
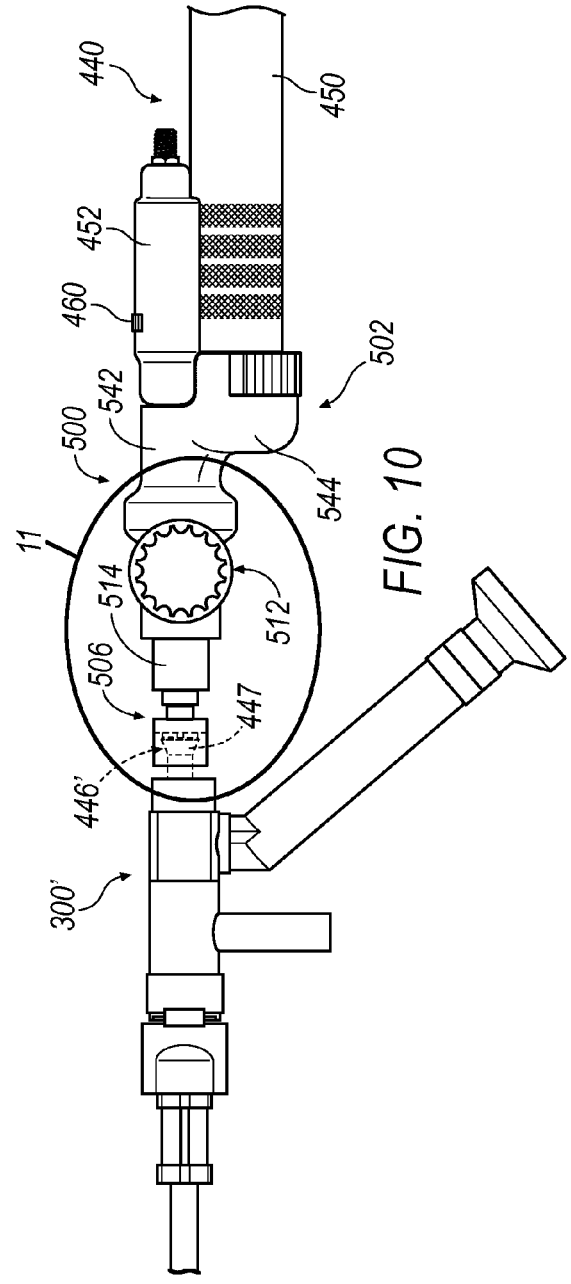

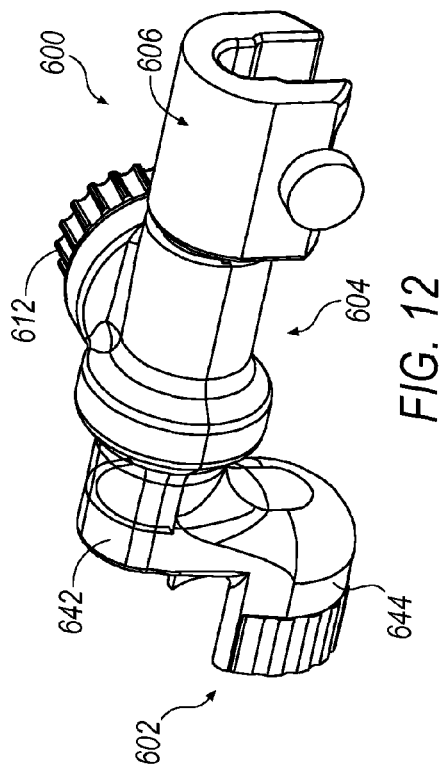
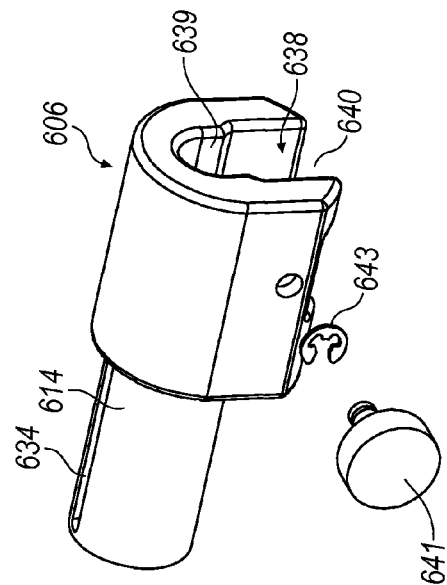
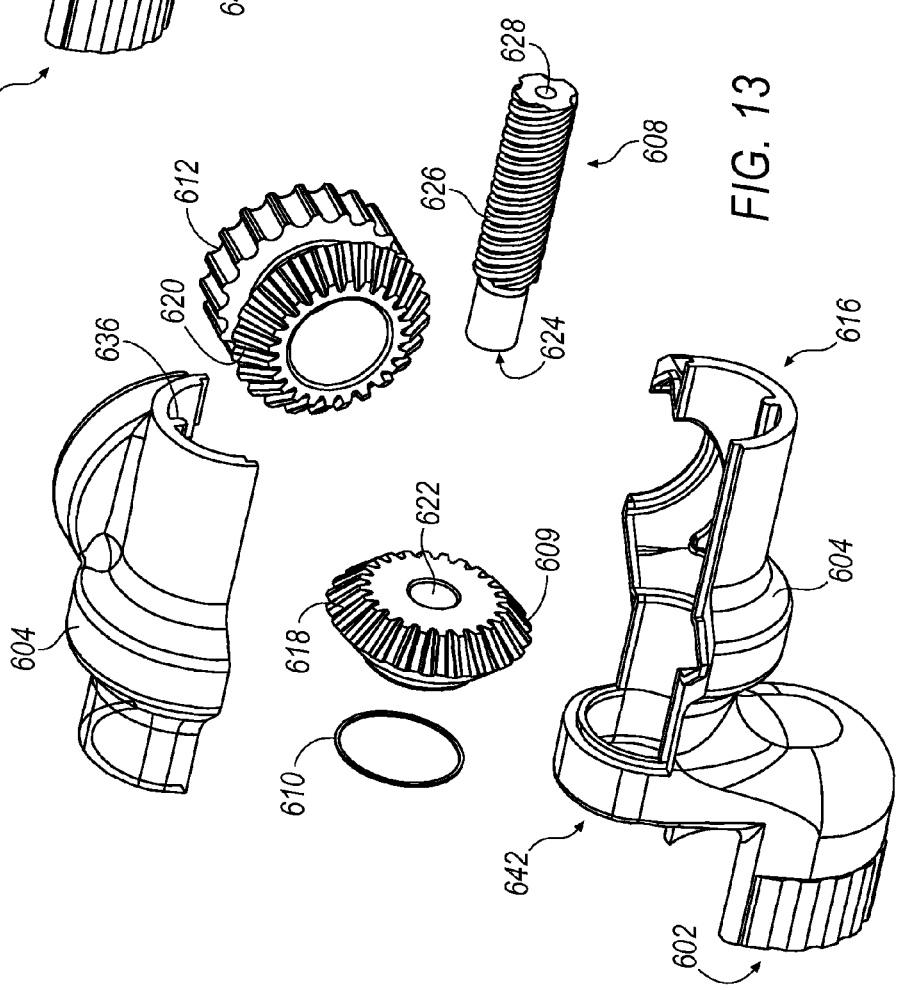
FIG. 12
FIG. 13

SURGICAL ADAPTER ASSEMBLY FOR USE WITH ENDOSCOPE

CROSS REFERENCE TO RELATED APPLICATIONS

This application claims priority to U.S. Provisional Patent Application No. 61/258,922, filed Nov. 6, 2010, the disclosure of which is incorporated by reference in their entirety.

TECHNICAL FIELD

The present disclosure relates generally to surgical adapters for introducing a surgical device into the body of a patient and, more particularly, to surgical adapters for use with delivering a surgical device through an endoscope.

BACKGROUND

Endoscopic surgery allows for surgery to be performed while reducing damage to the surrounding tissue as compared to open surgical procedures. An endoscope typically includes at least one working channel allowing insertion and deployment of various medical devices to the surgical site. The endoscope also provides visualization of the surgical site during the procedure.

Once the desired position of the surgical site is reached, a surgical instrument may be inserted through the working channel and protrude from the distal end of the working channel at the visualized surgical site. For example, in one exemplary arrangement, a surgical cutting device is introduced to excise tissue samples from the surgical site. Such a surgical cutting instrument generally requires connection to a handpiece that provides rotary or reciprocative (or both) motion to the cutting portion of the instrument. When the cutting operation is enabled, tissue is generally drawn through the mouth of the cutting instrument, severed, and removed from the surgical site.

Unfortunately, during the procedure the handpiece must be constantly controlled by the surgeon to control the extension of the instrument beyond the working channel of the endoscope. As such, the distal end of the surgical cutting device may move independently from the endoscope. Indeed, to control the placement of the surgical cutting device, typically a surgeon must continually manipulate both the endoscope and the surgical cutting device, relying on the surgeon's hand-eye coordination, to insure proper placement of the surgical cutting instrument, and to prevent inadvertent movement away from a selected area of interest or moving too deep into area, thereby causing unintended damage to surrounding tissues or structures. This constant control of the instrument causes fatigue in the surgeon and makes it difficult to hold the endoscope still while precisely controlling the surgical cutting instrument during the procedure.

Further, during an endoscopic procedure, at times it is necessary to selectively adjust the depth of the medical device within the surgical site in order to precisely target a lesion for removal. To this end, the cutting element must be accurately positioned adjacent the lesion. While conventional endoscopes allow for insertion of a surgical cutting device through the working channel, they do not provide for independently maintaining the position of the surgical cutting device with the endoscope.

Accordingly, a surgical adapter is needed that permit a surgical cutting device to be operatively connected to an endoscope, without requiring constant attention to fine hand-eye coordination. Further, a need exists for a surgical adapter that facilitates adjustable and fixed positioning of the device within the patient, removal of the device from the working channel, and reinsertion of the device through the working channel to a desired position.

BRIEF DESCRIPTION OF THE DRAWINGS

Exemplary embodiments of the present disclosure will now by described by way of example in greater detail with reference to the attached figures, in which:

FIG. 3 is a perspective view of an exemplary surgical cutting device;

FIG. 5 is perspective view of an exemplary surgical adapter for use with a surgical system;

FIG. 6 is an exploded view of the surgical adapter of FIG. 5;

FIG. 9 is a side view of the surgical sub-assembly of FIG. 8, as the sub-assembly is being operatively connected to a first type of endoscope.

FIG. 10 is a side view of the connected surgical sub-assembly of FIG. 8 operatively connected to the endoscope shown in FIG. 9.

FIG. 12 is a perspective view of an alternative embodiment of a surgical adapter for use with a surgical system;

FIG. 13 is an exploded view of the surgical adapter of FIG. 12;

DETAILED DESCRIPTION

Figure 1:
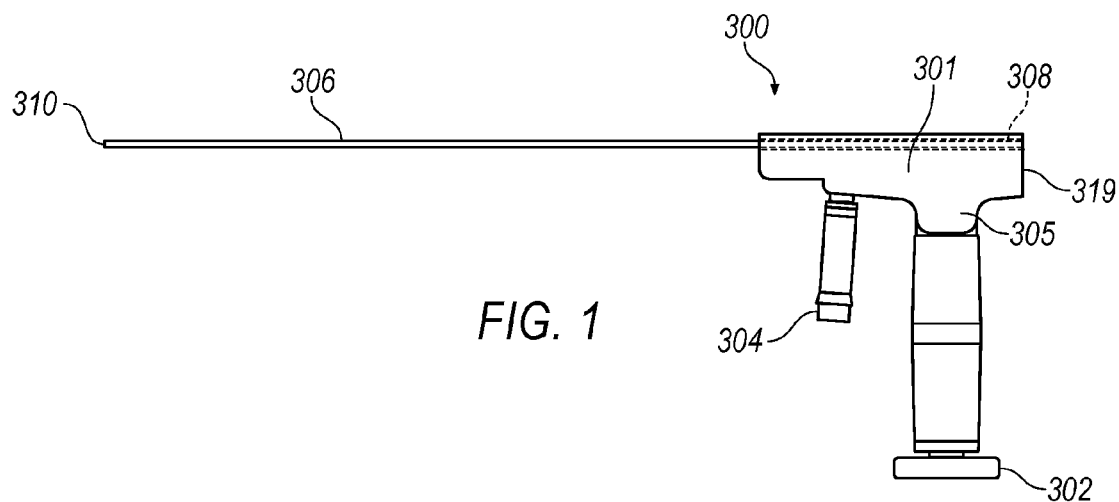
FIG. 1 is a side elevational view of an embodiment of an exemplary endoscope.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein are surgical systems that include surgical adapters for use with surgical devices that may be suited for neurosurgical applications, including, but not limited to, the removal of spine and brain tissue. The surgical systems of the present disclosure provide surgeons with an enhanced ability to control placement of a surgical device within a surgical site so as to effectively control the extent of tissue cutting, as well as the impact on surrounding tissue during tissue cutting procedures.

Endoscopes are used to visualize various areas of interest within a patient. Referring to FIG. 1, a first exemplary type of an endoscope 300 is depicted. Endoscope 300 comprises a housing 301, an eye-piece 302, a fiber optic light cable connector 304, and a shaft 306. Shaft 306 is defined by a proximal end 308 which is disposed in and connected to housing 301 and a distal end 310. As may be seen, distal end 310 is spaced apart from proximal end 308. Endoscope 300 is configured to allow a user to view a surgical area of interest proximate distal end 310 through eye-piece 302, when distal end 310 is inserted into a surgical site. As is conventional in the art, shaft 306 also includes a conduit (not separately shown) for transmitting light provided via fiber optic connector 304 to the surgical area. Shaft 306 may also include a lens (not separately shown) for magnifying and viewing the surgical area.

Eye-piece 302 is connected to housing 301. Eye-piece 302 may also be connected to a camera with a camera connector (not shown) so that the image generated by endoscope 300 can be viewed remotely on a display monitor.

Figure 2A:
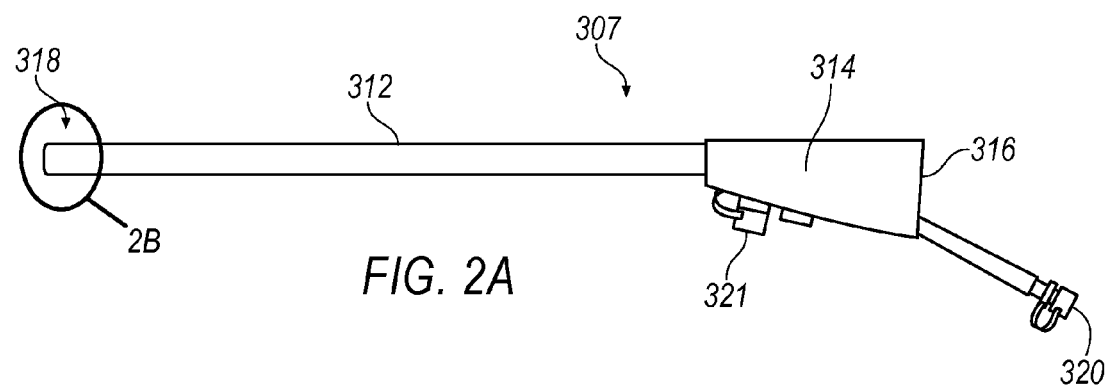
FIG. 2A is a side elevational view of an embodiment of a trocar for use with the endoscope of FIG. 1.
Figure 2B:
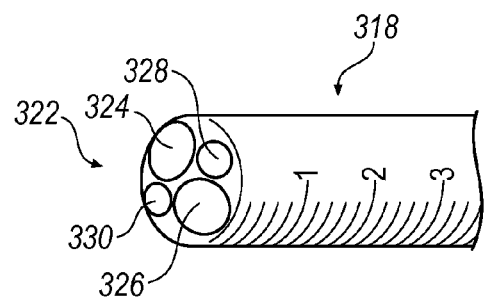
FIG. 2B is a detail view of a distal tip of the trocar of FIG. 2A.

To facilitate the use of endoscope 300 in surgical procedure, a trocar 307 may also be provided, as best seen in FIGS. 2A and 2B. Trocar 307 is especially useful for closed surgical procedures. Trocar 307 comprises a trocar body 314 and a trocar shaft 312. Trocar 307 is defined by a proximal end 316, with a proximal opening formed in trocar body 314, and a distal end 318 of shaft 312. Shaft 312 defines one or more channels in its interior. As shown in FIG. 2B, shaft 312 may have a plurality of channels, 324, 326, 328, and 330 which terminate at a tip distal face 322. In one embodiment, a working channel 324 is sized to accommodate an outer cannula 444 of a surgical cutting device 440 (to be described below in further detail). Channel 326 is sized to accommodate an endoscope shaft 306. Channel 328 may be configured as an irrigation channel used to direct irrigation fluid from an irrigation conduit 320 to the surgical site. Channel 330 may be configured as a relief channel used to relieve fluid pressure at the surgical site. During closed procedures, as irrigation fluid flows to a surgical site it can pressurize the site.

Referring to FIG. 3, an exemplary surgical cutting device 440 is shown, such as that disclosed in co-pending, and co-owned with the assignee of the present application, U.S. patent application Ser. No. 12/389,447, the contents of which are incorporated by reference in its entirety. Surgical cutting device 440 includes a handpiece 442 and a cutting element that includes an outer cannula 444 and an inner cannula (not shown). A distal end 447 of the cutting element is configured for insertion into a patient.

In one exemplary configuration, handpiece 442 is configured with a generally cylindrical shape. Handpiece 442 may be sized and shaped to be grasped with a single hand. Handpiece 442 also includes a lower housing 450 comprising a proximal section 446 and a distal section 448. A front housing section 455 may be connected to a cam housing positioned in distal section 448. An upper housing 452 is also provided. The cutting element is mounted to upper housing 452 and may be fluidly connected to a tissue collector 458. In one exemplary arrangement, tissue collector 458 may be operatively connected directly to upper housing 452. Alternatively, tissue collector 458 may be remotely connected to the cutting element by appropriate tubing. A vacuum line (not shown) may be connected to a proximal end of tissue collector 458 to direct tissue into the cutting element, as well as to deliver severed tissue to tissue collector 458. A rotation dial 460 for selectively rotating the outer cannula 444 with respect to handpiece 442 is also mounted to upper housing 452.

In certain examples, tissue cutting device 440 may be combined with an imaging device to define a surgical system 303 that is capable of simultaneously imaging and cutting a target tissue, such as tissue associated with a patient's neurological system. Because assembly 303 effectively combines both imaging and cutting operations into a single, integral device, it is particularly advantageous in performing closed procedures where a surgical access path is created percutaneously.

Figure 4:
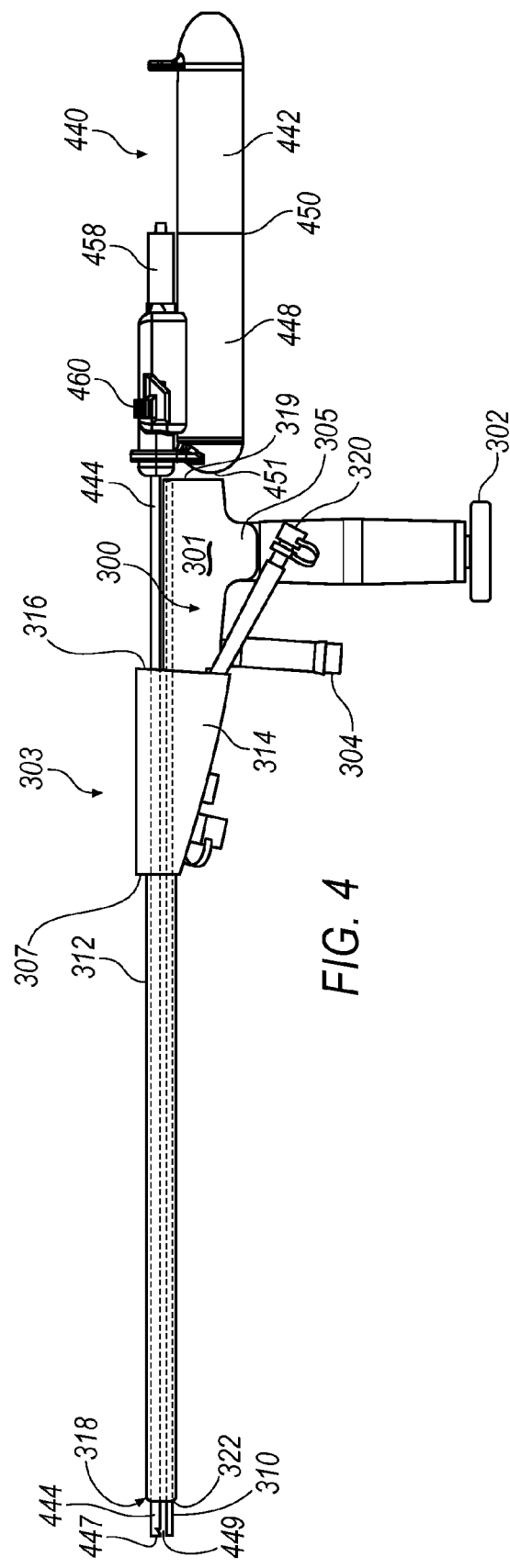
FIG. 4 is a side elevational view of an embodiment of a surgical system that includes an endoscope, a trocar and surgical cutting device.
Figure 7:
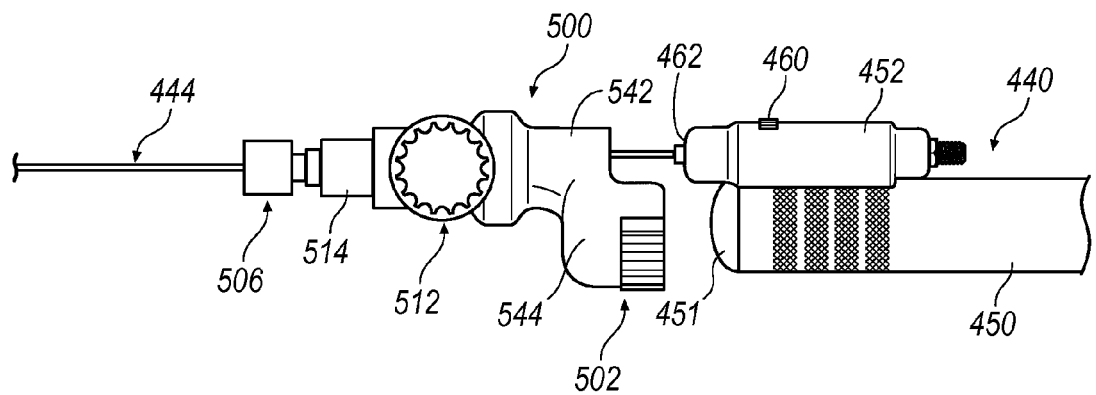
FIG. 7 is a partial side view of the surgical adapter of FIG. 5, as a surgical cutting device is being operatively connected thereto.

Referring to FIG. 4, an exemplary surgical system 303 is depicted. Surgical system 303 comprises a surgical cutting device, such as surgical cutting device 440, trocar 307, and an endoscope, such as endoscope 300. As shown in FIG. 4, endoscope 300 is inserted through trocar 307 via endoscope channel 326 (best seen in FIG. 2B) such that endoscope distal end 310 exits through, is flush with, or projects from trocar 307 at trocar shaft distal tip face 322. Surgical cutting device 440 is connected to trocar 307 such that outer cannula 444 of the cutting element is inserted in the open proximal end 316, through trocar body 314, and through working channel 324 of trocar shaft 312. Distal end 447 of the cutting element of surgical cutting device 440 projects through and away from shaft distal end 318 of trocar 307 at trocar shaft distal tip face 322.

Although various configurations are possible, in surgical system 303 of FIG. 4, tissue cutting device 440 is positioned with a proximal portion of outer cannula 444 adjacent to endoscope housing 301. Proximal end 319 of endoscope housing 301 is positioned distally of and adjacent to front housing 455 of surgical cutting device handpiece 442.

To use surgical assembly 303, a surgical access path is first created and/or the target tissue is accessed using an open procedure or a closed procedure. However, surgical assembly 303 is especially suited for closed procedures. In one exemplary example, the surgeon places one eye at eye-piece 302 and manipulates trocar shaft 312 to position distal trocar tip 318 proximate the target tissue. In another exemplary example, a camera is attached to eye-piece 302 and the surgeon views an image on a monitor that is connected to the camera. A vacuum level to be applied to device 440 is then set using panel controls on an attached surgical console. In one method, device 440 is configured to be gripped with a single hand so as to allow simultaneous manipulation of endoscope 300, trocar 307, and surgical cutting device 440. A variety of different grips may be used. In one example, surgical cutting device 440 is held like a writing instrument, with distal housing section 448 placed between the thumb and forefinger of one hand and proximal housing section 446 placed between the base of the forefinger and the base of the thumb. In another example, the thumb is placed on one side of distal housing section 448 and the forefinger is placed on top of upper housing 452 with proximal housing section 446 between the base of the thumb and forefinger. In yet another example, the proximal housing section 446 is gripped with the thumb placed adjacent proximal-most housing portion 442.

Depending on the selected hand and the surgeon's position with respect to that of the target tissue, dial 460 may be rotated to selectively rotate outer cannula 444 about its own longitudinal axis and to orient an outer cannula opening 449 immediately adjacent the target tissue. Surgical cutting device 440 is preferably configured such that when outer cannula 444 rotates, an inner cannula also rotates to maintain a fixed angular orientation between outer cannula 444 and the inner cannula. Once outer cannula opening 449 is in the desired position, a motor of surgical cutting device 440 is activated. In one example, the surgeon views the target tissue through eyepiece 302 to visualize the tissue's response (e.g., traction) to various levels of vacuum and selects a desired level.

Due to the application of vacuum, the target tissue proximate trocar distal end 318 is drawn into outer cannula opening 449. If desired, an irrigation fluid such as saline may be fed to the target tissue area via irrigation conduit 320 (shown in FIG. 2B).

Endoscope 300 is configured to allow a surgeon to view the target tissue through eye-piece 302. However, as discussed above, a camera may also be connected to a camera connector (not shown) attached to eyepiece 302 allowing the image generated by endoscope 300 to be viewed on a display monitor. In accordance with one example, the surgeon views the target tissue on the display monitor while manipulating surgical system 303 and cutting tissue.

In certain examples, surgical device 440 is configured such that its outer cannula 444 can be accommodated by working channels in known, industry standard sized trocars. For example, in certain embodiments, working channel 324 has an inner diameter of less than 8 mm, preferably less than 6 mm, more preferably less than 4 mm, and most preferably about 2 mm. However, it is understood that there may be other deices that include working channels 324 having an inner diameter even less than 2 mm. Outer cannula 444 is also configured with an outer diameter that allows outer cannula 444 to be slidably received in working channel 324. In other examples, outer cannula 444 is at least as long as known working channels. In certain embodiments, outer cannula 444 is at least about 6 inches, preferably at least about 8 inches, more preferably at least about 10 inches, and even more preferably at least about 12 inches in length.

Surgical assembly 303 is useful in a number of procedures, but is especially beneficial in closed procedures. In one exemplary method, surgical assembly 303 is used to perform closed, percutaneous tissue cutting procedures in the third ventricle of the brain. Such procedures include removing tumors and membranes in the third ventricle. In addition, cerebrospinal fluid circulates through the third ventricle and into the spinal column. In certain patients, occlusions can for in the third ventricle, blocking the fluid circulation. Surgical assembly 303 may be used to remove such occlusions and restore circulation. Other closed procedures for which surgical assembly is particularly well suited include the removal of tumors from the hypothalamus.

While surgical system 303 of FIG. 4 represents an advancement in surgical devices and procedures, there is no mechanism that suitably secures surgical cutting device 440 to endoscope 300. As such, distal end 447 of surgical cutting device 440 may move independently from shaft 312 of trocar 307. Accordingly, the surgeon must be sure to manipulate both trocar 307 and surgical cutting device 40 to insure proper placement of distal end 447 of surgical cutting device 440 to prevent distal end 447 from inadvertently moving away from an area of interest or moving too deep into the area of interest causing unintended damage to surrounding tissues and structures.

Specifically referring to FIGS. 5-12, to operatively connect surgical cutting device 440 to an alternative endoscope 350 configuration, a first exemplary embodiment of a surgical adapter 500 is provided. Surgical adapter 500 comprises a connecting portion 502, a housing portion 504 and an attachment mechanism 506. In one exemplary embodiment, housing portion 504 may be constructed of a first portion 504a and a second portion 504b that fit together, such as in a snap-fit arrangement. Housing portion 504 may house an advancing mechanism 508, a gear member 509 and a thrust washer or spring member 510. A dial member 512 is partially received within housing portion 504 and rotatably mounted thereto. A shaft member 514 is partially received within a distal end 516 of housing portion 504.

Gear member 409 is rotatably mounted within housing portion 504 and includes gear teeth 518 that mesh with gear teeth 520 mounted on dial member 512. A channel 522 is formed through gear member 509. A proximal end 524 of advancing mechanism 508 is fixedly received within channel 522. Advancing mechanism 508 further includes threads 526 formed on an outer surface thereof, and a receiving channel 528, both of which will be explained below in further detail.

A proximal end 530 of attachment mechanism 506 is secured to a distal end 532 of shaft member 514. Shaft member 514 further comprises at least one slot member 534 into which a tab member 536 (seen, for example, mounted on first portion 504a) from housing portion 504 is slidably received. In another exemplary configuration, shaft member 514 may comprise more than slot member 534 that mate with a plurality of corresponding tab members 536. In one exemplar configuration, tab members 536 are arranged in an opposing manner within housing portion 504. It is understood that various locations for tab members 536 on housing portion 504 are contemplated. It is also understood that other configurations for keying shaft member 514 to housing 504 are also contemplated.

Threads 526 operatively engage with threads formed on an internal surface of shaft member 514, to be explained in further detail below. Attachment mechanism 506 further includes a shaft member 538 and a cap member 540. Shaft member 538 defines a passageway 539 therethrough.

Figure 8:
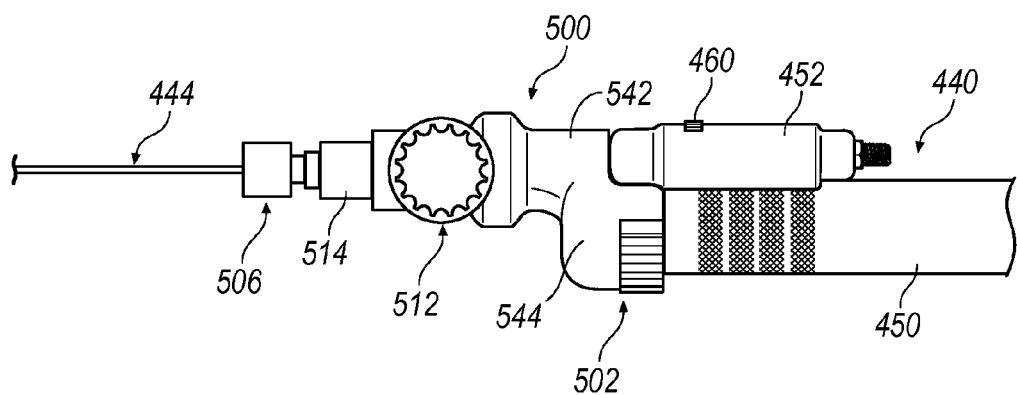
FIG. 8 is a partial side view of the surgical adapter of FIG. 5 with the surgical cutting device operatively connected thereto to form a surgical sub-assembly.
Figure 11:
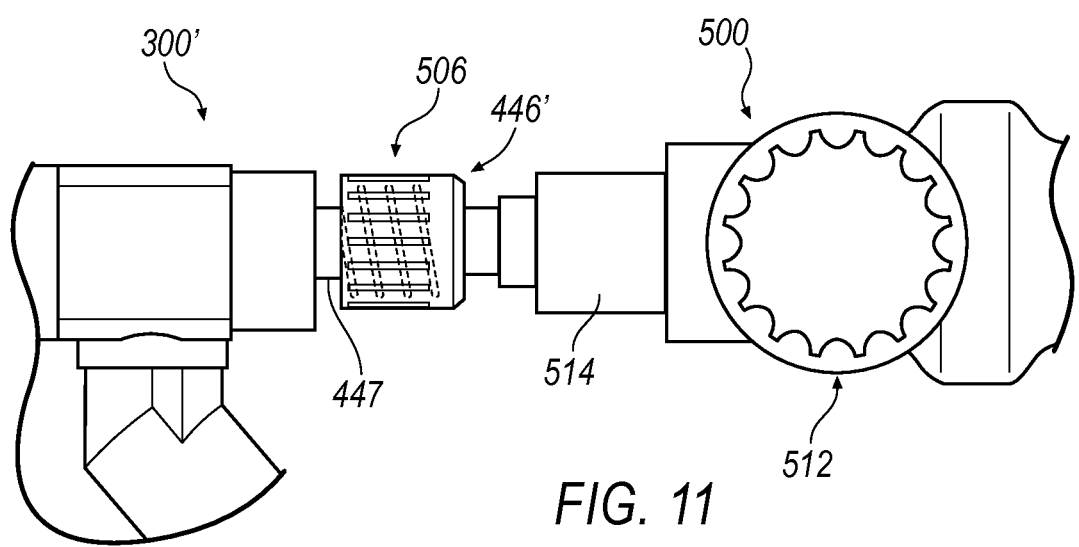
FIG. 11 is an enlarged view of encircled area 11 taken from FIG. 10.
Figure 14:
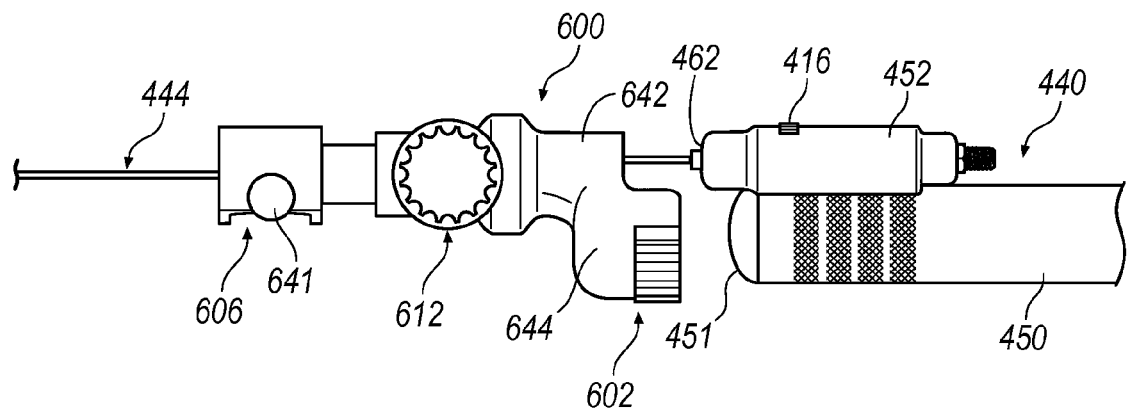
FIG. 14 is side view of the surgical adapter of FIG. 12 as a surgical cutting device is being operatively connected thereto.

Referring now to FIGS. 7-11, use of surgical adapter 500 will now be explained. First, distal end 447 (best seen in FIG. 3) of surgical cutting device 440 is inserted into surgical adapter 500. More specifically, distal end 447 of the cutting element of surgical cutting device 440 is inserted into a top portion 542 of connecting portion 502 and into receiving channel 528 of advancing mechanism and advanced through attachment mechanism 506. Top portion 542 further includes a mounting groove that receives a distal end 462 of upper housing 452 for frictional engagement. A bottom portion 444 of connecting portion 502 also includes a mounting groove that receives distal end 451 of lower housing 450 for frictional engagement, as shown in FIG. 8. In one exemplary embodiment, assembly of surgical adapter 500 to surgical cutting device 440 is performed at the factory prior to packaging and delivery of the devices. Further, to provide increased stability to the surgical system, distal end 451 may be fixedly connected to the mounting groove.

Once secured, distal end 447 of the cutting element of surgical cutting device 440 is then received in a proximal end 446' of an endoscope 300'. In one embodiment attachment mechanism 506 fixedly engages a portion 447 of endoscope 300', thereby securing tissue cutting device 440 to endoscope 300'. More specifically, attachment mechanism 506 is disposed around proximal end 446' such that proximal end 446' is received within endoscope receiving portion 540. Mounting groove member 538 is received within portion 447 of endoscope 300'.

However, in accordance with one aspect of the disclosure, the extent that distal end 447 may extend outwardly from a distal end of endoscope 300' may be selectively controlled by the surgeon. More specifically, dial member 512 may be selectively rotated in a first direction to advance distal end 447 of the cutting element of surgical cutting device 440 with respect to the distal end of endoscope 300'. Dial member 512 may be selectively rotated in a second direction to move distal end 447 of surgical cutting device 440 toward proximal end 446' of endoscope 300'.

Gear teeth 520 of dial member 512 mesh with gear teeth 518 of gear member 509 such that when dial member 512 is rotated, gear member 509 also rotates. Because proximal end 524 of advancing mechanism 508 is fixedly secured to gear member 509, as gear member 509 rotates, advancing mechanism 508 also rotates. Receiving channel 528 is sized to receive outer cannula 444. Thus rotation of advancing mechanism 508 causes shaft member 514 to move along tab member 536, effectively moving distal end 447 of the cutting element.

Because surgical adapter 500 secures surgical cutting device 440 to endoscope 300', the surgeon may better control the amount of extent of distal end 447 of outer cannula 444 to allow for safer, more secure, more stable and a more accurate placement of the cutting mechanism.

Referring to FIGS. 12-18, an alternative embodiment of a surgical adapter 600 is shown. Surgical adapter 600 is similar to surgical adapter 500 in that it comprises a connecting portion 602, a housing portion 604 and an attachment mechanism 606. In one exemplary embodiment, housing portion 604 is constructed of a first portion 604a and a second portion 604b that matingly fit together, such as in a snap-fit arrangement. Housing portion 604 may house an advancing mechanism 608, a gear member 609 and a wave washer or spring member 610. A dial member 612 is partially received within housing portion 604 and rotatably mounted thereto. A shaft member 614 is partially received within a distal end 616 of housing portion 604, similar to that which was described above in connection with surgical adapter 500.

Gear member 609 is rotatably mounted within housing portion 604 and includes gear teeth 618 that mesh with gear teeth 620 mounted on dial member 612. A channel 622 is formed through gear member 609. A proximal end 624 of advancing mechanism 608 is fixedly received within channel 622. Advancing mechanism 608 further includes threads 626 formed on an outer surface thereof, and a receiving channel 628, both of which will be explained below in further detail.

Attachment mechanism 606 is secured to a distal end of shaft member 614. Shaft member 614 further comprises at least one slot member 634 into which a tab member 636 from housing portion 604 is slidably received. Threads 626 operatively engage with threads formed on an internal surface of shaft member 614, to be explained in further detail below. Attachment mechanism 606 includes a mounting groove member 638 having a cannula receiving portion 639 and an endoscope receiving portion 640. A retaining member 641 is selectively engageable with attachment mechanism 606, to be explained below in further detail. A locking washer 643 may also be included.

Figure 15:
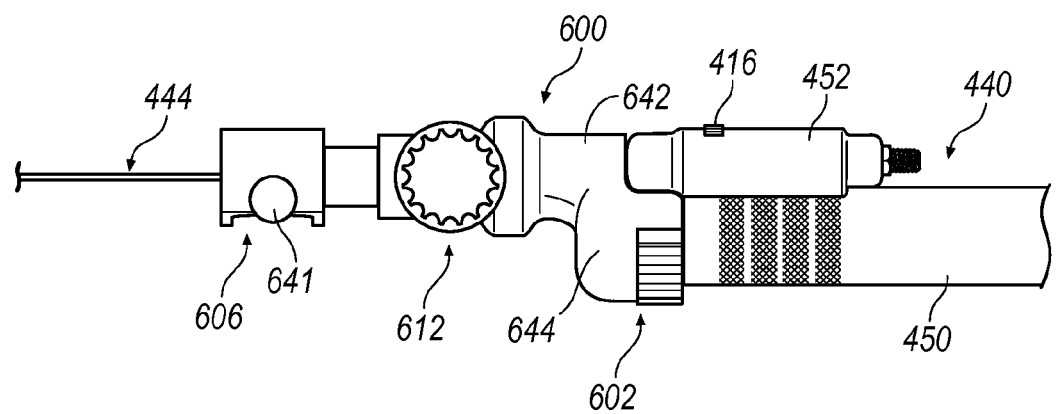
FIG. 15 is a side view of the surgical adapter of FIG. 12 with the surgical cutting device operatively connected thereto to form a surgical sub-assembly.
Figure 16:
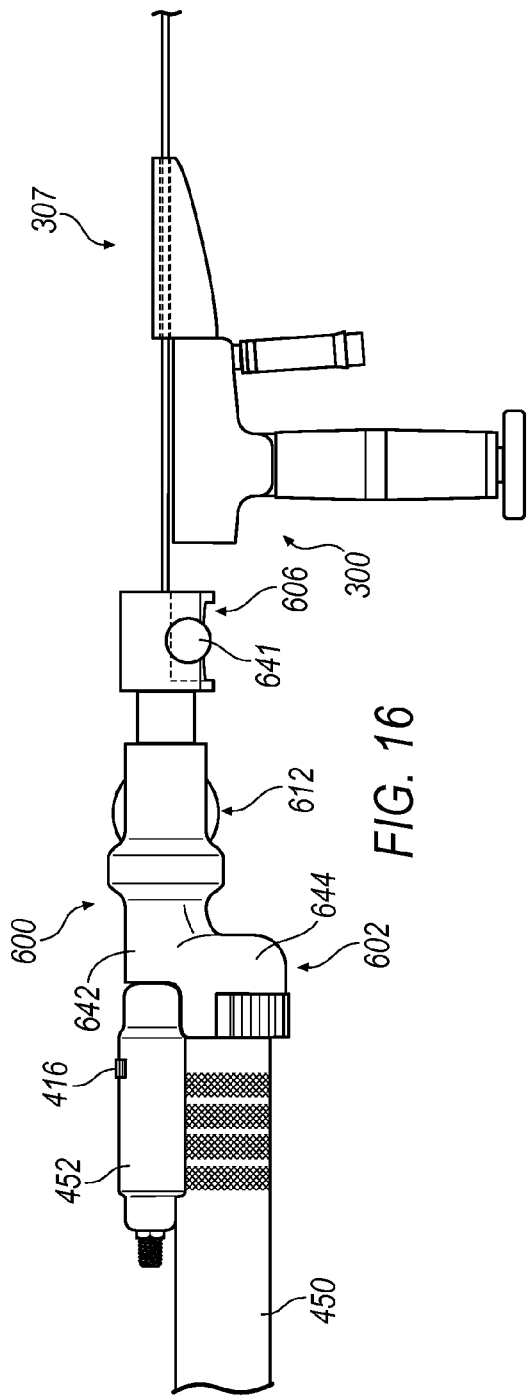
FIG. 16 is a side view of the surgical sub-assembly of FIG. 15 being operatively connected to the connected together endoscope and the trocar of FIGS. 1 and 2.
Figure 17:
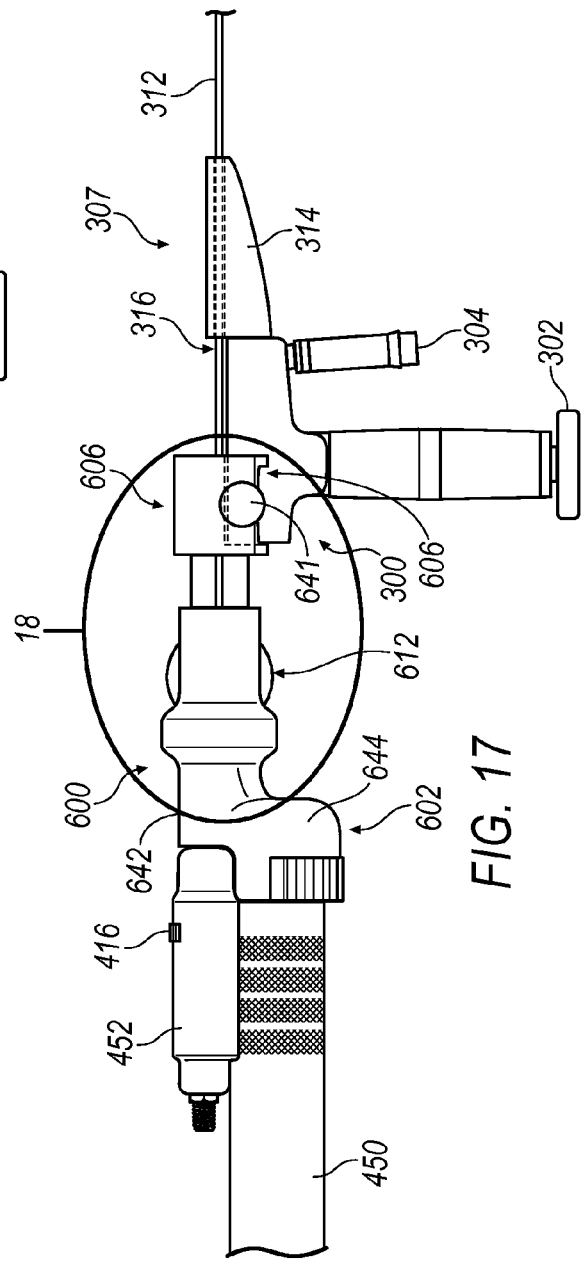
FIG. 17 if a side view of the connected surgical sub-assembly of FIG. 15 operatively connected to the connected together endoscope and trocar of FIGS. 1 and 2.
Figure 18:
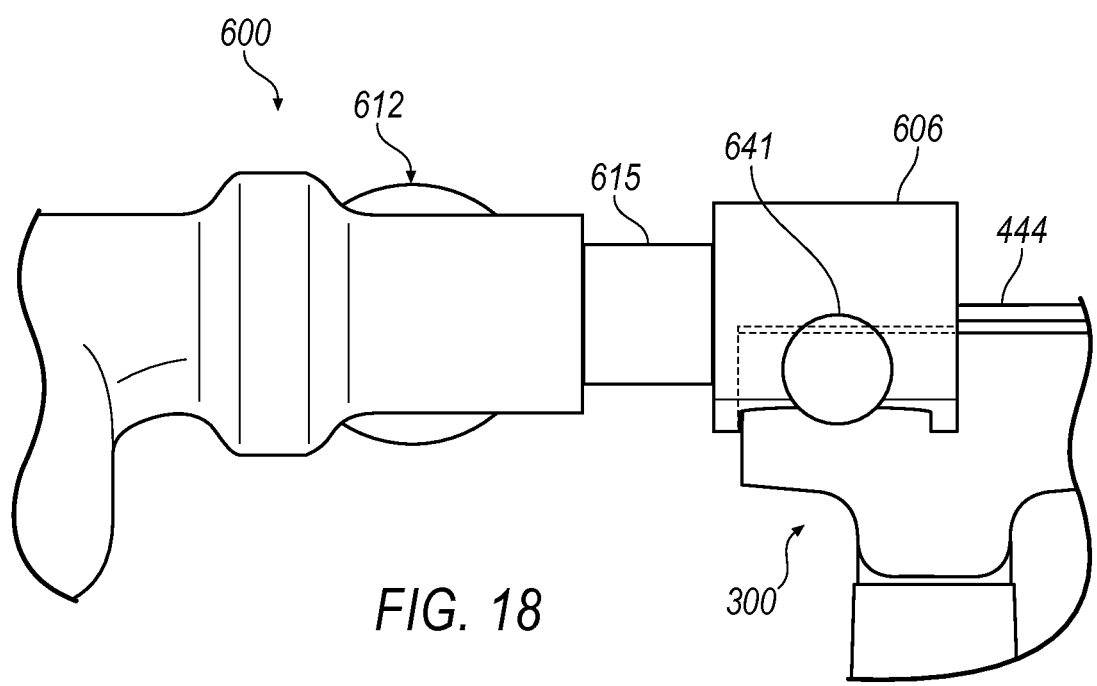
FIG. 18 is an enlarged view of encircled area 18 taken from FIG. 17.

Referring now to FIGS. 14-18, use of surgical adapter 600 will now be explained. First, distal end 447 (best seen in FIG. 3) of surgical cutting device 440 is inserted into surgical adapter 600. More specifically, distal end 447 of the cutting element of surgical cutting device 440 is inserted into a top portion 642 of connecting portion 602 and into receiving channel 628 and advanced through cannula receiving portion 639 of attachment mechanism 606. Top portion 642 includes a mounting groove that receives distal end 462 of upper housing 452 for frictional engagement. A bottom portion 644 of connecting portion 602 also includes a mounting groove that receives a distal end 451 of lower housing 450 for frictional engagement, as shown in FIG. 15. In one exemplary embodiment, assembly of surgical adapter 600 to surgical cutting device 440 is performed at the factory prior to packaging and delivery of the devices.

Once secured, distal end 447 of outer cannula 44 (and inner cannula positioned therein) is then received in proximal end 316 of trocar 307. In one embodiment attachment mechanism 606 fixedly engages a portion of endoscope 300, thereby securing surgical cutting device 440 to endoscope 300. More specifically, endoscope receiving portion 640 is sized to engage an outer surface of endoscope 300, leaving cannula receiving portion 639 open, but in general alignment with working channel 324. Once properly positioned, fastening mechanism 641 is actuated to frictionally attach attachment mechanism 606 to endoscope 300. Endoscope 300 is also attached to trocar 307, as described above. Thus, tissue cutting device 40 is also fixed with respect to trocar 307.

However, in accordance with one aspect of the disclosure, the extent that distal end 447 may extend outwardly from distal end face 322 of trocar 307 may be selectively controlled by the surgeon. More specifically, dial member 612 may be selectively rotated in a first direction to advance distal end 447 of outer cannula 444 of tissue cutting device 440 with respect to distal end face 322 of trocar 307. Dial member 612 may be selectively rotated in a second direction to move distal end 447 of outer cannula 444 toward trocar 307.

Gear teeth 620 of dial member 612 mesh with gear teeth 618 such that when dial member 612 is rotated gear mechanism 609 rotates. Because proximal end 624 of advancing mechanism 608 is fixedly secured to gear mechanism 609, as gear mechanism 609 rotates, advancing mechanism 608 also rotates. Receiving channel 628 is sized to receive outer cannula 444. Thus rotation of advancing mechanism 608 causes shaft member 614 to move along tab member 636, effectively moving distal end 447 of outer cannula 444.

Because surgical adapter 600 secures surgical cutting device 440 to endoscope 300, the surgeon may better control the amount of extent of distal end 447 of outer cannula 444 to allow for safer, more secure, more stable and more accurate placement of the cutting mechanism.

Referring to FIGS. 19-22, a surgical system 800 is depicted. Surgical system 800 comprises an endoscope 300", a surgical adapter 500 and a connector adapter 700. In one exemplary arrangement, endoscope 300" is a LOTTA® style endoscope distributed by the Karl Storz Endoscopy-America, Inc., El Segundo, Calif., and further includes a proximal end 446".

Connector adapter 700 comprises a shaft member 702, a proximal mounting member 704, a support member 706 and selectively engageable connecting members 708. A seal member 709 (best seen in FIG. 22) is secured to support member 706. Each connecting member 708 is operatively secured to support member 706 by a living hinge 710.

Connector adapter 700 provides a user with the ability to utilize a variety of instrumentation with endoscope 300", without requiring any permanent modifications to endoscope 300" or to the instrumentation by a user in the field, or by the manufacturer of endoscope 300". Moreover, connector adapter 700 is configured to provide a selectively attachable sealed interface between a working channel of endoscope 300" and a surgical instrument such as, for example, the NICO MYRIAD® manufactured and distributed by Nico Corporation of Indianapolis, Ind.

More specifically, shaft member 702 is fixedly mounted to support member 706. A working channel 712 extends through support member 706 and shaft member 702. Mounting member 704 may be secured to a proximal end of shaft member 702. In one exemplary configuration, mounting member 704 is configured as a flange member. However, it is understood that other mounting elements may also be provided including, but not limited to, threaded engagements.

Figure 21:
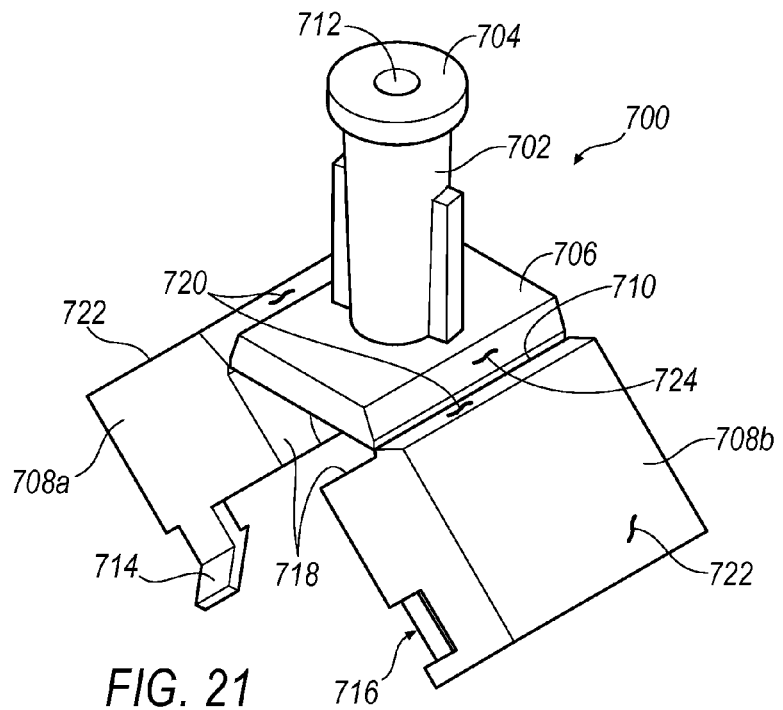
FIG. 21 is a perspective view of the connector adapter shown in the surgical system illustrated in FIG. 19.

As discussed above, connector adapter 700 further includes connecting members 708. In one exemplary arrangement, connecting members 708 are arranged in an opposing manner, as shown in FIG. 21. In one exemplary arrangement, connecting adapter 700 includes at least two connecting members 708a, and 708b. First connecting member 708a is configured with at least one selectively depressible locking tab 714. Second connecting member 708b is configured with a corresponding number of receiving grooves 716. Locking tabs 714 are configured to be selectively received and retained within corresponding receiving grooves 716 when connector adapter 700 is mounted to a surgical system, as will be explained in further detail below.

In operation, surgical adapter 500 is attached to a surgical cutting instrument such as that discussed above in connection with FIG. 3. Mounting member 704 of connector adapter 700 is then connected to cap member 540 of surgical adapter 500 such that shaft member 538 (best seen in FIG. 6 above) is received within working channel 712. Mounting member 704 is configured to engage with a corresponding mounting feature formed in cap member 540. For example, an internal surface of cap member 540 may be configured with frictional members that secure mounting portion 704 therein. Alternatively, as discussed above, both cap member 540 and mounting portion 704 may be provided with corresponding threads such that a threaded attachment may be achieved.

Once mounting portion 704 is secured to surgical adapter 500, connector adapter 700 is brought into engagement with a proximal end 446" of endoscope 300" such that seal member 709 engages proximal end 446". Seal member 709 is also configured with an opening therethrough (not shown) that is axially aligned with working channel 712 of shaft member 702. Seal member 709, which is constructed of a suitable sealing material to achieve a fluid-tight seal, is also configured so as to have a circumference that is at least as large as a circumference of an entrance piece to proximal end 446" of endoscope 300".

Figure 22:
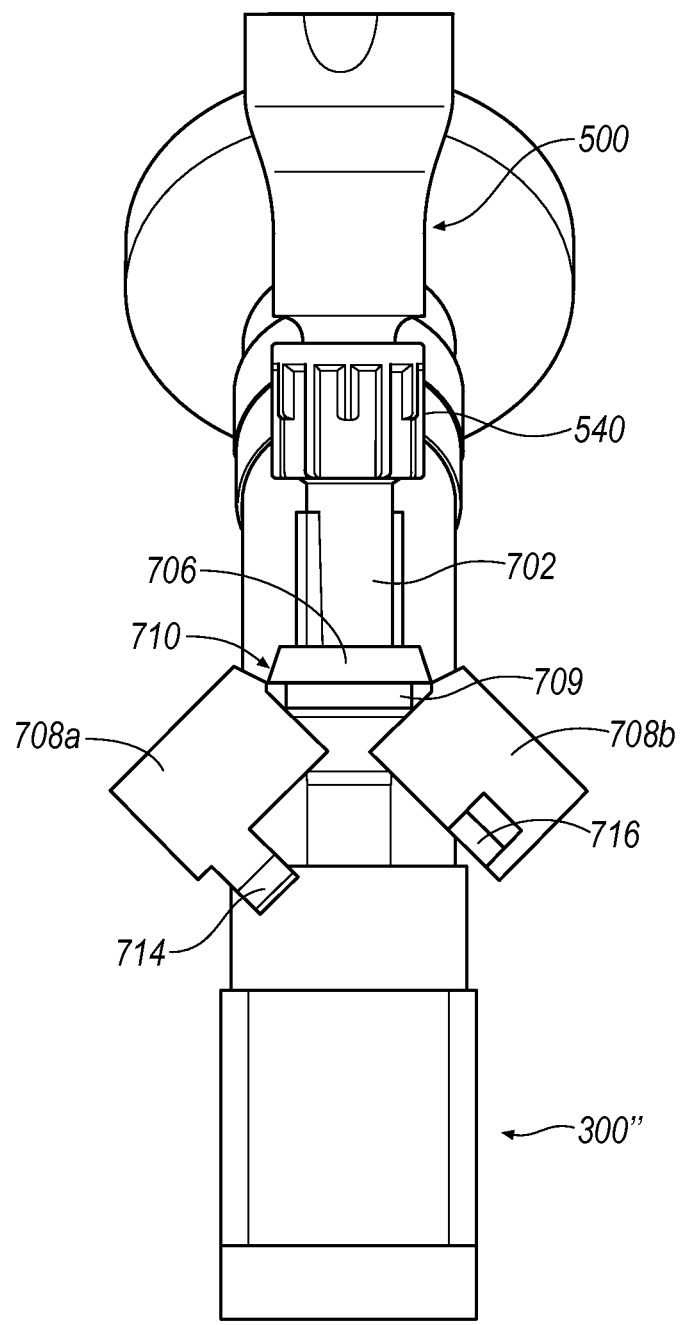
FIG. 22 is a top plan perspective, as the connector adapter is being secured to the endoscope shown in FIG. 19.

When seal member 709 is initially brought into engagement with proximal end 446" of endoscope 300", first and second connecting member 708a and 708b oriented toward support member 706 such that connecting members 708a, 708b are separated form one another, as shown in FIGS. 21 and 22. In other words, first and second connecting members 708a and 708b pivoted about living hinges 710.

Figure 19:
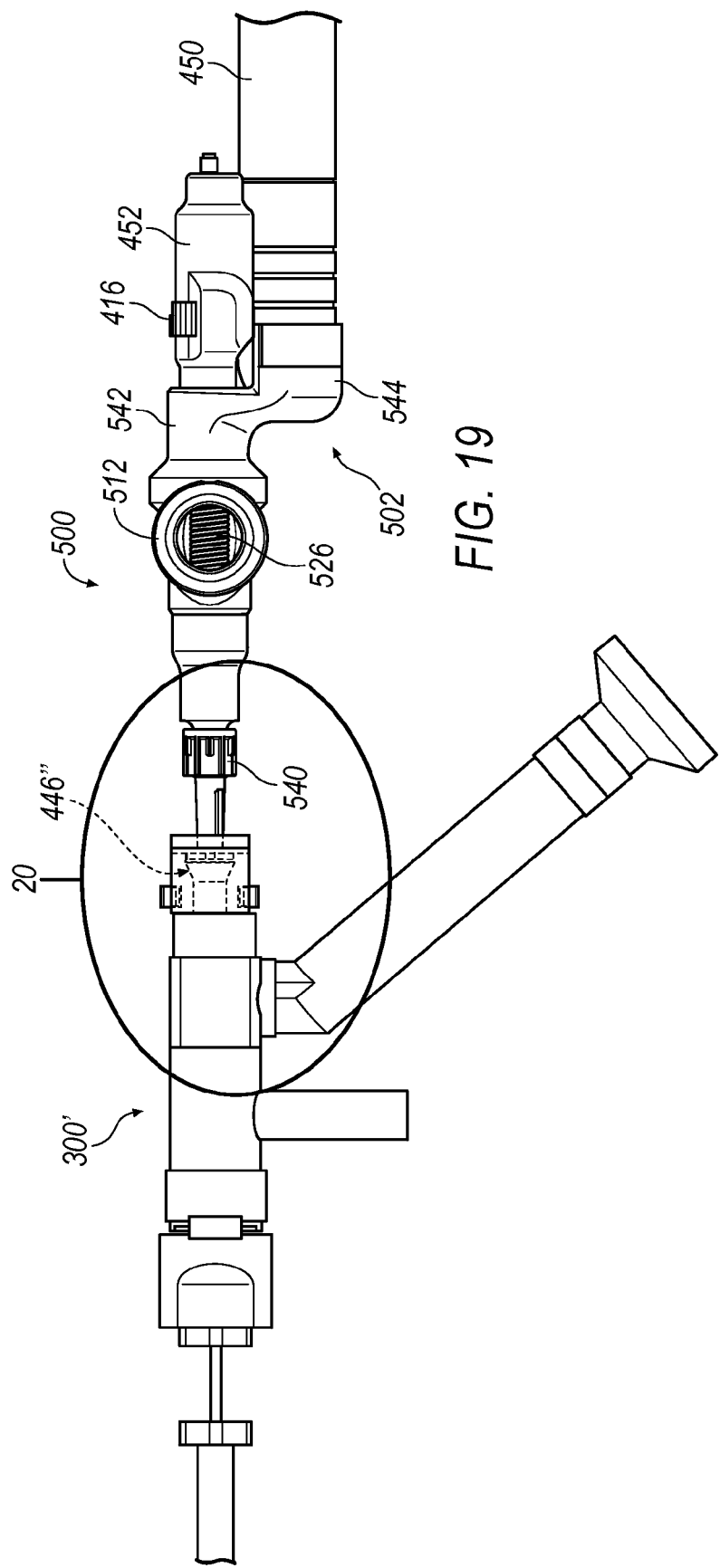
FIG. 19 is a side view of another embodiment of a surgical system including a connector adapter for use with the surgical adapter of FIG. 5, an endoscope, and a surgical cutting device.
Figure 20:
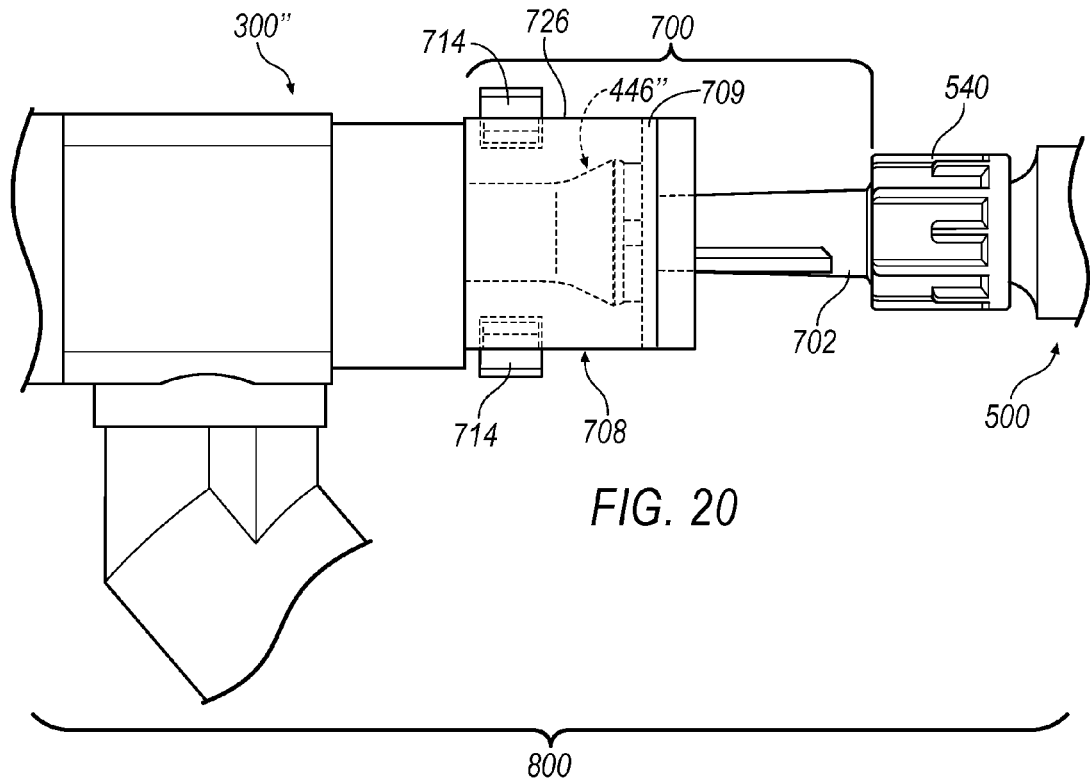
FIG. 20 is an enlarged view of encircled area 20 taken from FIG. 19.

In one exemplary configuration, first and second connecting members 708a, 708b are each configured with a mount surface 718 that mates with seal member 709 when first and second connecting members 708a, 708b are in a connected position (as shown in FIGS. 19-20). Connecting members 708a, 708b each may also be provided with an angled contacting face 720 that extends from living hinge 710 to an outer surface 722 of each connecting member 708a, 708b. Angled contacting face 720 is configured with cooperate with a corresponding angled contacting face 724 disposed on either side of support member 706.

Once seal member 709 engaged with proximal end 446" of endoscope 300", connecting members 708a, 708b are then pivoted toward one another so as to surround and mate to proximal end 446" of endoscope 300". Locking tabs 714 are then engaged with receiving grooves 716 so as to lock connecting members 708a, 708b quickly and easily together, thereby securing connector adapter 700 onto endoscope 300". Once the medical procedure is completed, connector adapter 700 may be selectively detached from endoscope 300" by simply depressing a portion of locking tabs 714 that is disposed externally from an outer surface 726 of connector adapter 700 (best seen in FIG. 20) to release locking tabs 714 form retaining grooves 716.

Figure 24:
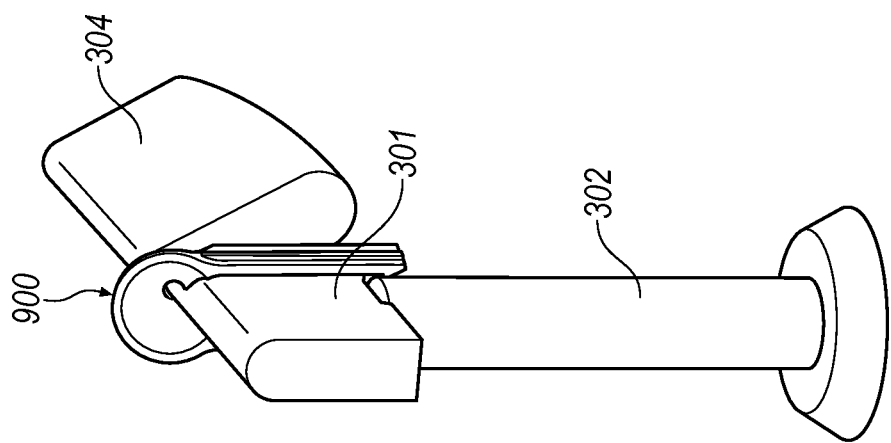
FIG. 24 is a partial perspective view of the funnel attachment of FIG. 23 operatively attached to an endoscope.
Figure 23:
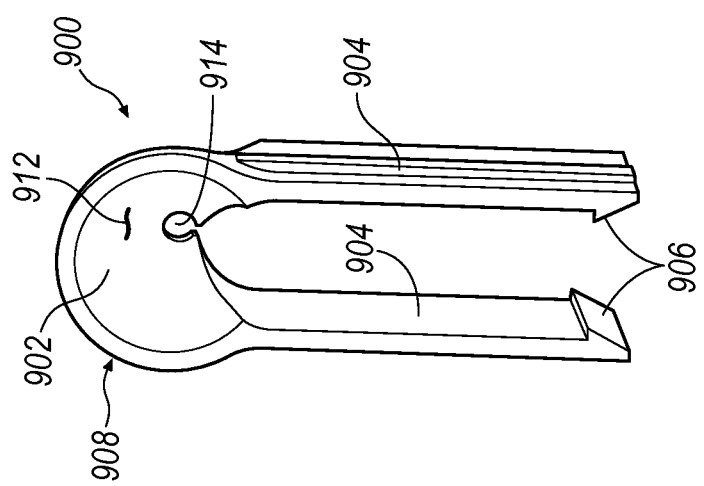
FIG. 23 is a perspective view of a funnel attachment for use with an endoscope.
Figure 25:
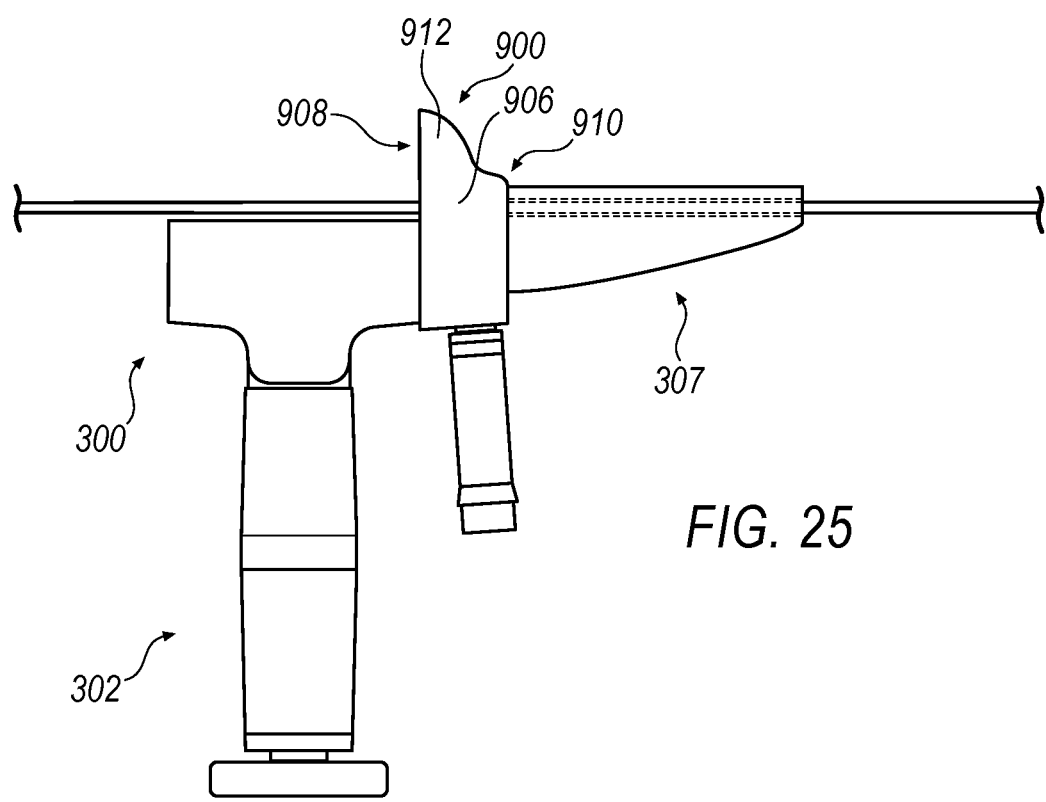
FIG. 25 is a side view of the funnel attachment of FIG. 23 attached to the endoscope as a working channel of the surgical cutting device is being inserted therein.

Referring to FIGS. 23 and 24, a funnel attachment 900 designed to direct distal end 447 of a cutting element from a surgical cutting instrument, such as cutting instrument 440, into a working channel 328 of trocar 307 is shown. During a surgical procedure, when a distal end of trocar 307 is positioned within a patient, the surgeon is viewing the surgical field, either through eyepiece 302 or on a display monitor. Thus, while the surgeon is viewing the surgical area, the surgeon may also be trying to insert distal end 447 into working channel 328 blindly. This approach often results in multiple frustrating attempts at trying to locate the opening of working channel 328 for receiving the outer cannula or other surgical component, and cause the loss of efficiency and valuable operating time.

To address this concern, funnel attachment 900 is provided. Funnel attachment 900 comprises a directing portion 902 and leg members 904. Leg members 904 are configured to fit over a housing 301 of an endoscope 300 and abut up against a proximal end of trocar 307. Feet members 906 extending from leg members 904 engage a bottom surface of housing 301 to secure funnel attachment 900 thereto.

Funnel attachment 900 is further defined by a proximal side 908 and a distal side 910. Directing portion 902 is defined by a funnel-like surface 912 that tapers toward a directing groove 914. When funnel attachment 900 is secured to endoscope 300, directing portion 902 is positioned such that directing groove 914 generally aligns with working channel 328 of trocar 307. Thus, as the surgeon is viewing the surgical area, the funnel-like surface 912 will serve to direct distal end 447 of an outer cannula 44 of a surgical cutting instrument 440 into directing groove 914, resulting in outer cannula 444 being correctly placed within working channel 328.

While funnel attachment 900 is not shown in use with surgical adapters 500, 600 or connector adapter 700, it is understood that funnel attachment 900 may be used with all of these components.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

The invention claimed is:

1. A surgical adapter for connecting a medical instrument to an endoscope, the surgical adapter comprising:
   a housing portion configured with a distal attachment portion; and
   an advancing assembly at least partially disposed within the housing portion, the advancing assembly having a selectively operable rotating member, an advancing shaft, and a shaft connector;
   wherein a proximal end of the distal attachment portion is operably connected to the shaft connector and a distal end member configured to be operably attached to a proximal portion of an endoscope; and
   wherein the advancing shaft is rotatably received within the shaft connector and wherein the shaft connector is non-rotatably mounted within the housing portion via an axial engagement slot formed within a body of the shaft connector, wherein the axial engagement slot is configured for receiving at least one corresponding axial tab member formed in the housing portion such that the tab member may slide axially along the engagement slot;
   wherein the surgical adapter is configured such that a portion of a medical instrument is receivable within the housing portion so as to be operably engaged with the advancing assembly such that the advancing assembly may be selectively actuated to selectively rotate the advancing shaft within the shaft connector so as to axially move a distal end of the medical instrument with respect to the endoscope.

2. The surgical adapter of claim 1, wherein the distal end member further includes a shaft member extending therethrough, the shaft member defining a passageway through which the portion of the medical device may extend.

3. The surgical adapter of claim 1, wherein the rotating member includes a gear member, a dial member, and an advancing shaft, wherein the gear member is mounted for rotational movement within the housing portion, the dial member is mounted to engage with the gear member, and the advancing shaft is fixedly secured to the gear member.

4. The surgical adapter of claim 3, wherein the advancing assembly further comprises one of a wave spring member and thrust washer that serves to bias the advancing assembly.

5. The surgical adapter of claim 3, wherein the shaft connector is fixedly positioned within the housing portion.

6. The surgical adapter of claim 1, wherein the distal attachment portion is defined by a mounting groove member that is selectively engageable with the proximal portion of the endoscope.

7. The surgical adapter of claim 6, wherein the distal attachment portion is fixedly connected to the shaft connector.

8. The surgical adapter of claim 6, wherein the rotating member includes a gear member, a dial member, and an advancing shaft, wherein the gear member is mounted for rotational movement in a first direction, the dial member is mounted to engage with the gear member, and the advancing shaft is fixedly secured to the gear member.

9. The surgical adapter of claim 8, wherein the advancing assembly further comprises one of a wave spring member and thrust washer that serves to bias the advancing assembly.

10. A surgical adapter for connecting a medical instrument to an endoscope, the surgical adapter comprising:
    a housing portion configured with a distal attachment portion;
    wherein the distal attachment portion is defined by a proximal end and a distal cap member, wherein the distal cap member may be selectively engaged with a proximal portion of an endoscope;
    an advancing assembly at least partially disposed within the housing portion, the advancing assembly having a selectively operable rotating member, an advancing shaft, and a shaft connector, wherein the proximal end of the distal attachment portion is operably connected to the shaft connector on one end;
    wherein the advancing shaft is rotatably received within the shaft connector and wherein the shaft connector is non-rotatably mounted within the housing portion via an axial engagement slot formed within a body of the shaft connector, wherein the axial engagement slot is configured for receiving at least one corresponding axial tab member formed in the housing portion such that the tab member may slide axially within the engagement slot; and
    wherein the surgical adapter is configured such that a portion of a medical instrument is receivable within the housing portion so as to be operably engaged with the advancing assembly such that the advancing assembly may be selectively actuated to selectively rotate the advancing shaft within the shaft connector so as to axially move a distal end of the medical instrument with respect to the endoscope.

11. The surgical adapter of claim 10, wherein the rotating member includes a gear member, a dial member, and an advancing shaft, wherein the gear member is mounted for rotational movement within the housing portion, the dial member is mounted to engage with the gear member, and the advancing shaft is fixedly secured to the gear member.

12. The surgical adapter of claim 11, wherein the advancing assembly further comprises one of a wave spring member and thrust washer that serves to bias the advancing assembly.

13. The surgical adapter of claim 11, wherein the shaft connector is fixedly positioned within the housing portion.

14. The surgical adapter of claim 10, wherein the cap member further includes a shaft member extending therethrough, the shaft member defining a passageway through which the portion of the medical device may extend.

15. The surgical adapter of claim 10, wherein the distal attachment portion is defined by a mounting groove member that is selectively engageable with the proximal portion of the endoscope.

16. The surgical adapter of claim 15, wherein the distal attachment portion is fixedly connected to the shaft connector.

17. A surgical assembly comprising:
- a surgical adapter comprising:
  - a housing portion configured with a distal attachment portion; and
  - an advancing assembly at least partially disposed within the housing portion, the advancing assembly having a selectively operable rotating member, an advancing shaft, and a shaft connector, wherein a proximal end of the distal attachment portion is operably connected to the shaft connector on one end;
- wherein the advancing shaft is rotatably received within the shaft connector and wherein the shaft connector is non-rotatably mounted within the housing portion via an axial engagement slot formed within a body of the shaft connector, wherein the axial engagement slot is configured for receiving at least one corresponding axial tab member formed in the housing portion such that the tab member may axially slide within the engagement slot;
- an endoscope having a proximal portion, the proximal portion is configured to be operably attached to the distal attachment portion of the surgical adapter; and
- a medical instrument having a distal end, the distal end configured to be received by the housing portion of the surgical adapter so as to be operably engaged with the advancing assembly such that the advancing assembly may be selectively actuated to selectively rotate the advancing shaft within the shaft connector so as to axially move the distal end of the medical instrument with respect to the endoscope.

\* \* \* \* \*